United States Patent [19]

Ueda

[11] Patent Number: 4,776,844
[45] Date of Patent: Oct. 11, 1988

[54] MEDICAL TUBE

[75] Inventor: Yasuhiro Ueda, Tokyo, Japan

[73] Assignee: Olympus Optical Co., Ltd., Tokyo, Japan

[21] Appl. No.: 41,713

[22] Filed: Apr. 23, 1987

[30] Foreign Application Priority Data

May 2, 1986 [JP] Japan .................................. 61-102463
Jul. 15, 1986 [JP] Japan .................................. 61-164817

[51] Int. Cl.$^4$ ........................................... A61M 25/00
[52] U.S. Cl. ..................................... 604/95; 604/281; 128/6
[58] Field of Search ..................... 128/4, 6–8, 128/348.1, 656–658, 772; 604/93, 95, 281, 282, 264, 280

[56] References Cited

U.S. PATENT DOCUMENTS

| | | | |
|---|---|---|---|
| 1,060,665 | 5/1913 | Bell | 604/281 |
| 2,583,298 | 1/1952 | Kowan | 604/281 |
| 3,890,977 | 6/1975 | Wilson | 604/281 |
| 4,427,000 | 1/1984 | Ueda | 128/6 |
| 4,543,090 | 9/1985 | McCoy | 128/657 |
| 4,601,283 | 7/1986 | Chikama | 128/4 |
| 4,676,229 | 6/1987 | Krasnicki | 604/282 |

FOREIGN PATENT DOCUMENTS 59-2344  1/1984  Japan .
59-48710 3/1984  Japan .

Primary Examiner—Dalton L. Truluck
Assistant Examiner—Frank Wilkens
Attorney, Agent, or Firm—Frishauf, Holtz, Goodman & Woodward

[57] ABSTRACT

A medical tube used as an insertion section of a catheter for angiography or of an endoscope. The medical tube has a flexible tube, and an elastic member embedded in the peripheral wall of the tube, for keeping the tube straight. The elastic member is formed of a high-elastic alloy whose transformation temperature at which the alloy transforms in phase from the martensite structure to the austenite structure is set at a temperature lower than that at which the medical tube is used. When the medical tube used as the insertion section of a catheter or endoscope is inserted into a living body, it is prevented from being buckled, or bent easily at the same portion after a long use. The durability of the insertion section is therefore improved, and organs in the living body are in no way damaged when the insertion section is inserted.

12 Claims, 5 Drawing Sheets

MEDICAL TUBE

BACKGROUND OF THE INVENTION

The present invention relates to a medical tube which is inserted into a living body, and more particularly to a medical tube used as an insertion section of a catheter for angiography or as an insertion section of an endoscope.

The insertion section of a catheter or endoscope is, when inserted into a living body, apt to be buckled due to the resistance acting against the inserting action. If such a catheter or endoscope is repeatedly used, its insertion section will be permanently bent.

Thus, if the insertion section of a catheter or endoscope is buckled or permanently bent when inserted, force is not properly transmitted from an operating section of the catheter or endoscope to the insertion section, thereby degrading the operational characteristic. If the insertion section buckled at a portion thereof is inserted into a blood vessel, the buckled portion will damage the peripheral wall of the vessel. With such an insertion section having a poor operational characteristic, the time for which the insertion section need be inserted will inevitably be longer, which will increase the patient's pain.

In order to facilitate the insertion of a medical tube for angiography, a stainless wire or plate may be embedded in the peripheral wall of the tube. However, the stainless material has a small elastic region with respect to stress. If a stress exceeding the elastic region is applied to the tube, the tube will be buckled and will be permanently bent after a long use.

The medical tube used as the insertion section of a catheter or endoscope, described above, is inserted into a blood vessel, alimentary canal, etc., so as to examine or treat the affected part. The tube should therefore be inserted into a blood vessel, alimentary canal, etc. without damaging the same. Further, a medical tube is needed which permits the distal end portion thereof to be curved in a desired direction at a desired part in the living body.

Conventionally, various medical tubes whose distal end portion can be curved are known, e.g., from Japanese Patent Disclosure (KOKAI) No. 59-48710 and Japanese Utility Model Disclosure (KOKAI) No. 59-2344. According to the prior art structures, a shape memory alloy arranged in the medical tube is deformed by heat applied thereto, whereby the distal end portion of the tube is curved.

However, the shape memory alloy arranged in the tube does not assume a preset shape at a normal room temperature and has a martensite structure wherein it can be plastically deformed by an external force. The tube will therefore be easily buckled due to the plastic deformation of the shape memory alloy. If the buckled tube is inserted through a blood vessel, alimentary canal, etc., it would damage the organ.

SUMMARY OF THE INVENTION

The object of the present invention is to provide a medical tube which can be easily inserted into a living body without being buckled or permanently bent. The invention provides a medical tube using a shape memory alloy as a driving member, wherein the tube is prevented from being buckled or permanently bent as a result of the plastic deformation of the shape memory alloy.

The object can be achieved by the medical tube of the invention. The medical tube has a flexible tube, and an elastic member embedded in a wall of the flexible tube for keeping the tube straight. The elastic member is formed of a high-elastic alloy whose transformation temperature at which the alloy transforms in phase from a martensite structure to an austenite structure is set at a temperature lower than that at which the medical tube is used.

According to one embodiment of the invention, a driving member is provided in the flexible tube for curving the tube body, in addition to the above structure. The driving member includes a shape memory alloy which assumes a preset shape when heated.

The medical tube of the invention, used as an insertion section of a catheter or endoscope, is not buckled when inserted into a living body, or permanently bent after a long use. The durability of the insertion section is therefore remarkably improved. At the same time, it is possible to prevent the living body from being damaged due to the abnormal deformation of the insertion section. Besides, when the insertion section is inserted into the living body, the tube is allowed to be deformed easily along the configuration of an organ to be examined, whereby the insertion section can be inserted into the living body easily and smoothly. Further, it is possible to shorten the time required for the examination or treatment using a catheter or endoscope, thereby reducing the patient's pain.

DETAILED DESCRIPTION OF THE PREFERRED EMBODIMENTS

Figure 1:
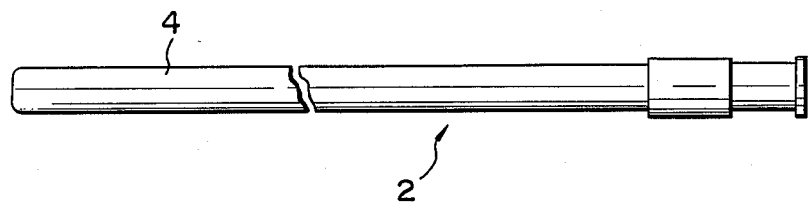
FIG. 1 is a side view of a catheter provided with a medical tube according to a first embodiment of the invention.
Figure 2:
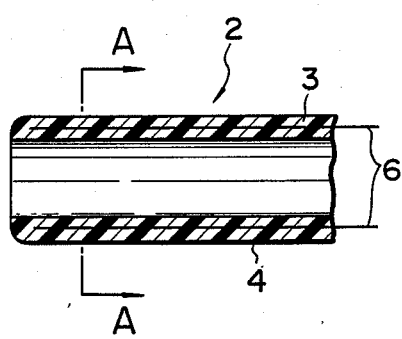
FIG. 2 is a longitudinal sectional view of a distal end portion of the catheter shown in FIG. 1.
Figure 3:
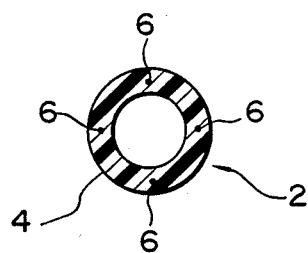
FIG. 3 is a cross-sectional view of the distal end portion, taken along line A—A in FIG. 2.

FIGS. 1 to 3 show a medical tube according to a first embodiment of the invention.

In this embodiment, the invention is applied to a catheter for use in angiography. Catheter 2 includes insertion section 4 formed by a flexible tube 3. Four straight core bars 6 are embedded in the peripheral wall of insertion section 4 equidistantly along the circumference thereof, and extend longitudinally of insertion section 4. Core bars 6 are each formed of a high-elastic alloy. The transformation temperature at which the high-elastic alloy transforms in phase from a martensite structure to an austenite structure is set at a temperature lower than that at which the catheter is used.

Figure 4:
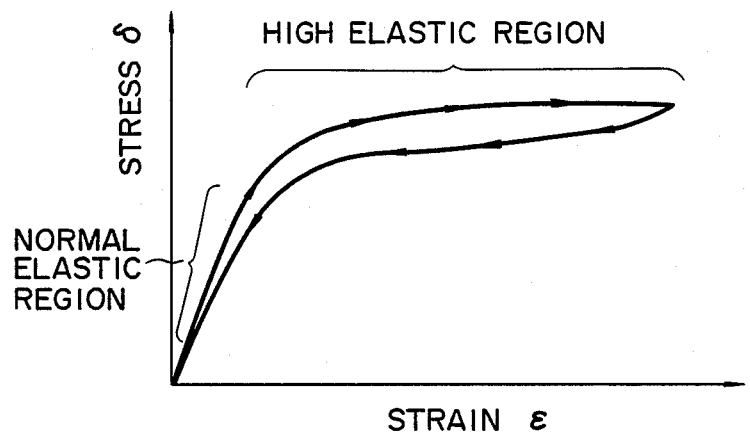
FIG. 4 is a graph showing the relationship between stress acting upon a core bar formed of a high-elastic material and strain produced in the same.

The "high-elastic alloy" is an alloy which exhibits high-elasticity at a predetermined temperature, such as a Ti-Ni alloy (Ti-51 atomic % Ni) and Cu-Zn-Al alloy (Cu-23 atomic % Zn-4 atomic % Al). The Ti-Ni alloy is preferable in practice. The high-elastic alloy has a composition generally similar to that of a shape memory alloy (SMA), but exhibits high-elasticity at a temperature higher than the transformation temperature (more accurately, transformation end point Af) at which the alloy transforms in phase from a low-temperature or martensite structure to a high-temperature or austenite structure. FIG. 4 shows a stress-strain characteristic of the high-elastic alloy. As will be understood from the characteristic curves in FIG. 4, the high-elastic alloy has an elastic property wherein, even if strain is produced in the alloy to a degree corresponding to the plastic region of ordinary metal, the alloy becomes free from the strain when relieved from stress, whereby no strain remains in the alloy. If transformation point Af is set at a temperature lower than a normal room temperature, e.g., lower than 0° C., the high-elastic alloy exhibits its high-elasticity at a room temperature or bodily temperature. For example, the Ti-Ni alloy (Ti-51 atomic % Ni) maintains its high-elastic property against as much as 4% of strain produced therein.

In catheter 2 for use in angiography, insertion section 4 as a whole exhibits high-elasticity due to the provision of core bars 6 in insertion section 4. Even when catheter 2 is inserted through a blood vessel, it is in no way buckled, or easily bent at the same portion after a long use. The operational characteristic of the catheter is therefore improved.

As will be understood from FIG. 4, due to the high-elasticity of core bars 6, strain is increased with an almost equal stress in a region beyond the predetermined level. In other words, both large and small deformations can be produced with an almost equal force applied to insertion section 4 of catheter 2. As a result, when insertion section 4 is inserted through a winding blood vessel, insertion section 4 is deformed according to the winding of the blood vessel. Therefore, only a relatively small force is necessary for moving insertion section 4 forward.

The first embodiment uses four core bars 6 embedded in insertion section 4. Alternatively, only one core bar 6 may be embedded in insertion section 4. Further, core bar 6 may not be arranged along the whole length of insertion section 4. It may be arranged only in a necessary portion, or be divided into a plurality of sections to be arranged in several portions of insertion section 4.

Figure 5:
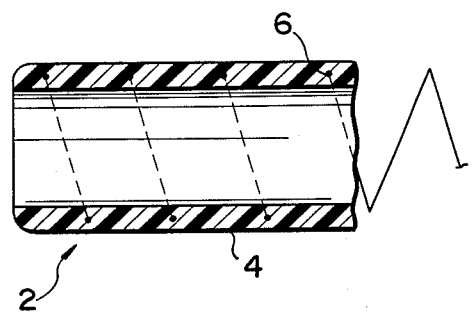
FIG. 5 is a longitudinal sectional view of a distal end of a tube according to a modification of the first embodiment.

FIG. 5 shows a modification of the medical tube according to the first embodiment. In FIG. 5, only one coiled core bar 6 is used which is embedded in the peripheral wall of insertion section 4. Also in this modification, insertion section 4 of catheter 2 utilizes the property of the high-elastic alloy.

Figure 6:
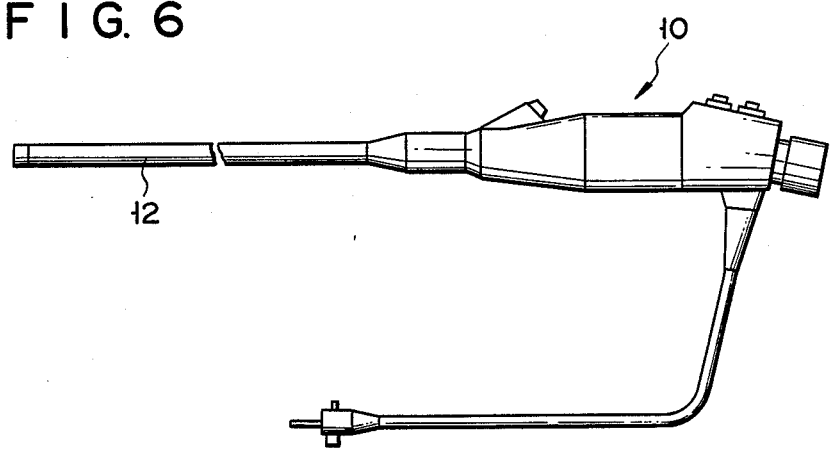
FIG. 6 is a side view of a cardiovascular endoscope provided with a medical tube according to a second embodiment of the invention.
Figure 7:
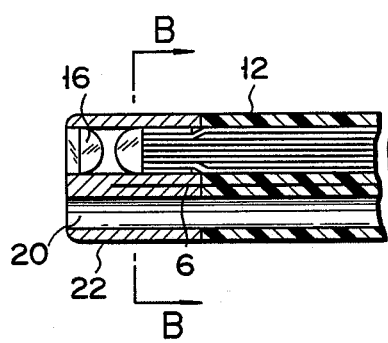
FIG. 7 is a longitudinal sectional view of an insertion section of the endoscope shown in FIG. 6.
Figure 8:
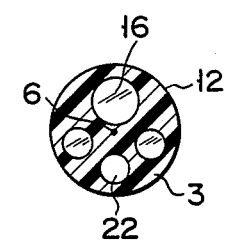
FIG. 8 is a cross-sectional view of the insertion section, taken along line B—B in FIG. 7.

A medical tube according to a second embodiment of the invention will now be described with reference to FIGS. 6 to 8.

In the second embodiment, core bar 6 formed of a high-elastic alloy is applied to insertion section 12 of cardiovascular endoscope 10. As shown in FIG. 7, straight core bar 6 formed of a high-elastic alloy is embedded in insertion section 12 of cardiovascular endoscope 10 along the length thereof.

Insertion section 12 is circular in section and has a multi-lumen structure wherein a plurality of passages (i.e., lumens) are formed through a solid resin body 3. Insertion section 12 has objective optical system 16 arranged in distal end 22. Image-guide fiber 18 is connected to the base of objective optical system 16. Channel 20, through which a medical instrument is inserted, is formed through insertion section 12. Reinforcing tube 24 is arranged around the outer periphery of the base portion of insertion section 12, for preventing section 12 from being buckled or bent. Core bar 6, formed of a high-elastic alloy, has one end secured to distal end 22, and the other end secured to an operating section, not shown, of the endoscope. The diameter of core bar 6 is greater in a portion located within tube 24 than in the other portion thereof.

The insertion section of the endoscope according to the second embodiment is prevented from being buckled, or permanently bent after a long use, like the case of the first embodiment.

A typical cardiovascular endoscope is, when inserted through a blood vessel, apt to be buckled at a portion thereof near the distal end of reinforcing tube 24, due to the inserting action. In this embodiment, core bar 6 formed of a high-elastic alloy is arranged in insertion section 12 and has a greater diameter in a portion at which insertion section 12 is likely to be buckled. As a result, the insertion section of the endoscope is prevented from being buckled, thereby facilitating the insertion of section 12.

Figure 9:
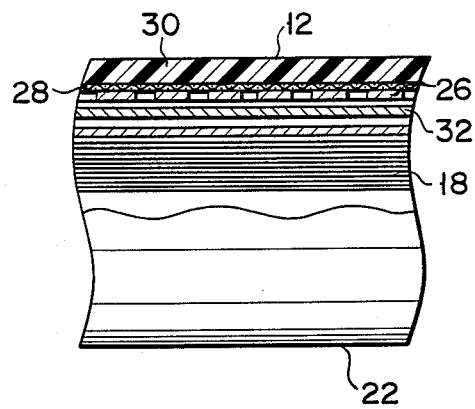
FIG. 9 is a partially sectional view of a tube according to a modification of the second embodiment.

FIG. 9 shows a modification of the medical tube according to the second embodiment.

Insertion section 12 of endoscope 10 includes flex 26 formed of a high-elastic alloy. Flex 26 has its outer periphery covered with net-like tube 28 and covering member 30. Angle wire 32, image-guide fiber 18, etc., are arranged inside flex 26.

Due to the high-elasticity of flex 26, insertion section 12 is prevented from being buckled, or permanently bent after a long use, thereby improving the operational characteristic of insertion section 12.

Figure 10:
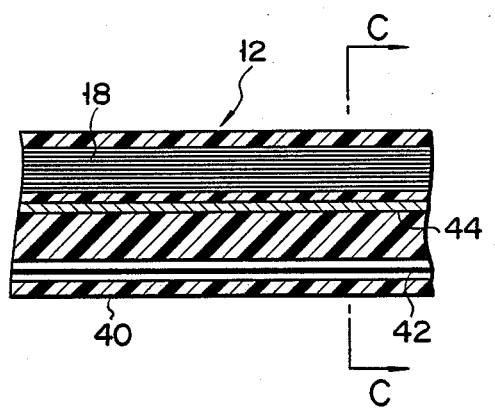
FIG. 10 is a longitudinal sectional view of an insertion section of an endoscope provided with a medical tube according to a third embodiment of the invention.
Figure 11:
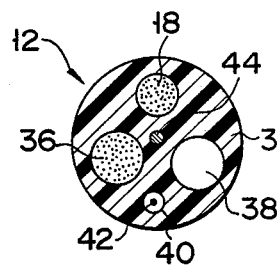
FIG. 11 is a cross-sectional view of the insertion section, taken along line C—C in FIG. 10.
Figure 12:
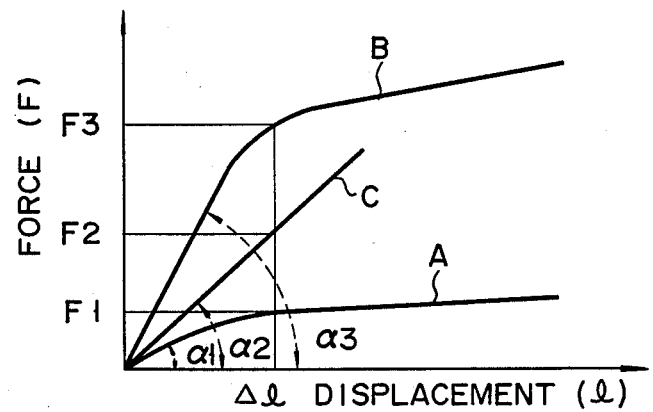
FIG. 12 is a graph showing the relationship between force acting upon a driving member and displacement of the same, and similar relationship concerning an elastic member, obtained by the third embodiment.

A medical tube according to a third embodiment of the invention will now be described with reference to FIGS. 10 to 12. FIGS. 10 to 12 show insertion section 12 of an endoscope to which a medical tube according to the third embodiment is applied. Insertion section 12 comprises a multi-lumen tube 3 formed of polyurethane resin or silicon resin. Inside the tube are arranged image-guide fiber 18 and a light-guide fiber 36 extending along the whole length of insertion section 12. Channel 38, through which a medical instrument is inserted, and fluid passage 40 extend along the whole length of insertion section 12. Driving member 42, formed by a wire made of a shape memory alloy, is inserted through passage 40. A predetermined curved shape is memorized in driving member 42. Driving member 42 has a crystal structure of martensite phase in a temperature range including room temperature and bodily temperature, and has a crystal structure of austenite phase as a basic phase at a temperature above transformation temperature Af. Transformation temperature Af between the martensite and austenite phases, i.e., the temperature at which the transformation to the austenite phase completes, is set at 50° C., for example.

Fluid passage 40 has one end opening in the distal end face of insertion section 12, and the other end connected to a fluid-supply connector provided in an operating section, not shown, of the endoscope.

Straight wire-like elastic member 44, formed of a high-elastic alloy having an austenite structure at a normal temperature or a piano wire, is embedded in insertion section 12 along the axial center thereof. Elastic member 44 extends along approximately the whole length of insertion section 12. Elastic member 44 has an elastic property as shown in FIG. 12. In the graph, the ordinate represents force F, and the abscissa represents displacement l. Curve A in FIG. 12 shows the characteristic of driving member 42 maintained at a temperature equal to a bodily temperature, and curve B shows the characteristic of the same member maintained at a high temperature. Straight line C shows the characteristic of elastic member 44. As will be understood from the graph, force F2 required to displace elastic member 44 by Δl is greater than force F1 required to displace driving member 42 maintained at a low temperature by Δl, and is smaller than force F3 required to displace driving member 42 maintained at a high temperature by Δl. As a result, while driving member 42 is maintained at a low temperature, insertion section 12 is kept straight by elastic member 44. On the other hand, when driving member 42 is kept at a high temperature, the deforming force exerted by driving member 42 overcomes the elasticity of elastic member 44, whereby insertion section 12 is curved. In FIG. 12, the inclination angles of curves A and B and straight line C are in the relationship $\alpha 3 > \alpha 2 > \alpha 1$.

In this embodiment, driving member 42 is heated by warm water (e.g., 50° C.) supplied to fluid passage 40.

According to insertion section 12 of the endoscope having the structure described above, driving member 42 formed of a shape memory alloy can be plastically deformed by an external force when maintained at a low temperature. However, since elastic member 44 is also arranged in insertion section 12, such plastic deformation is corrected by the elasticity of elastic member 44. In this manner, insertion section 12 is prevented from being buckled, or permanently bent after a long use.

In order to curve insertion section 12, driving member 42 is heated above transformation temperature Af, by supplying warm water to fluid passage 40.

Figure 13:
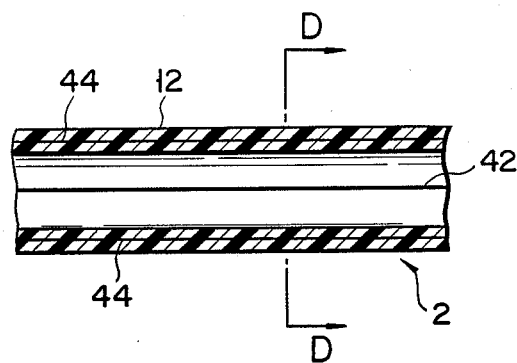
FIG. 13 is a longitudinal sectional view of a medical tube according to a first modification of the third embodiment.
Figure 14:
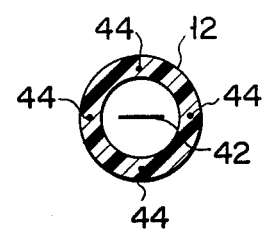
FIG. 14 is a cross-sectional view of the tube, taken along line D—D in FIG. 13.

FIGS. 13 and 14 show a first modification of the medical tube according to the third embodiment. The medical tube is applied to cardiovascular catheter 2. Elastic members 44 are four wires, such as piano wires and stainless wires, embedded in the peripheral wall of catheter 2 equidistantly along the circumference thereof. Band-like driving member 42 is arranged along the axial center of insertion section 12.

Figure 15:
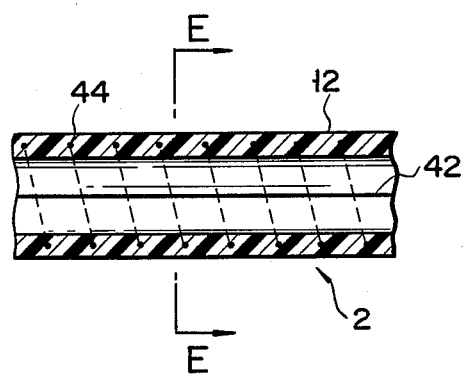
FIG. 15 is a longitudinal sectional view of a medical tube according to a second modification of the third embodiment.
Figure 16:
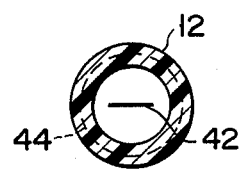
FIG. 16 is a cross-sectional view of the tube, taken along line E—E in FIG. 15.

FIGS. 15 and 16 show a second modification of the medical tube, wherein coiled elastic member 44 is embedded in the peripheral wall of catheter 2.

Figure 17:
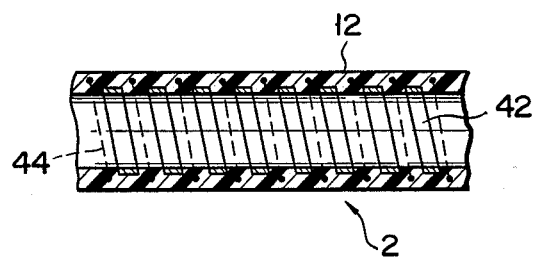
FIG. 17 is a longitudinal sectional view of a medical tube according to a third modification of the third embodiment.

FIG. 17 shows a third modification of the medical tube. As shown in the figure, driving member 42 and elastic member 44 are both coil-shaped and embedded in the peripheral wall of catheter 2.

Figure 18:
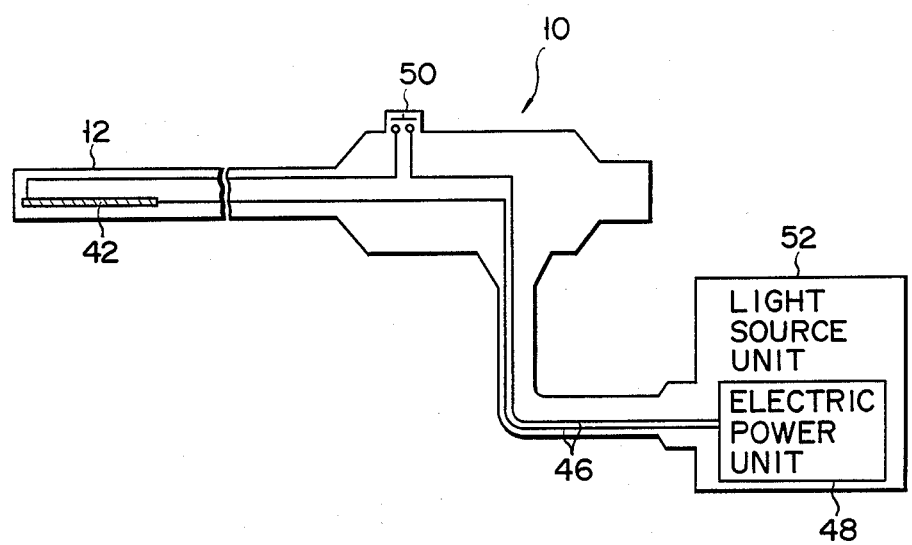
FIG. 18 is a side view schematically showing a driving member arranged in the endoscope, and an electric power unit.
Figure 19:
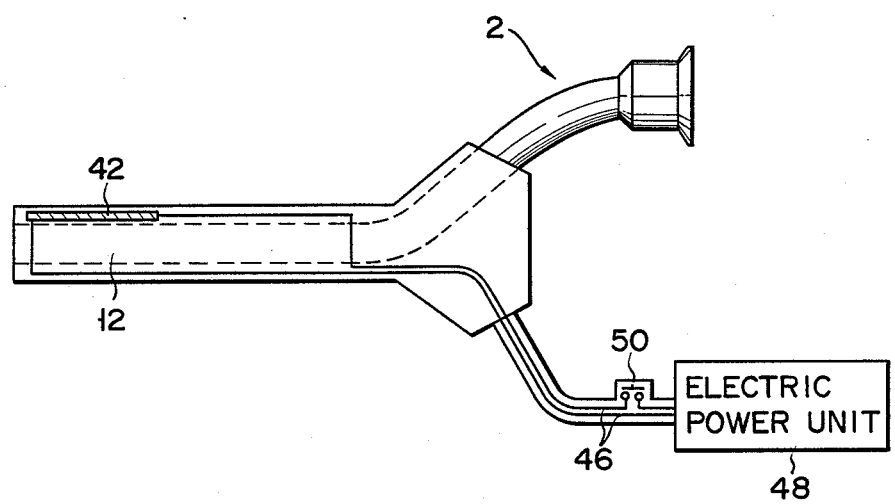
FIG. 19 is a side view schematically showing a driving member arranged in the catheter for use in angiography, and an electric power unit.

The present invention is not limited to the embodiments or modifications described above. For example, an electric current, instead of warm water, may be supplied to the driving member, so as to heat the member. FIGS. 18 and 19 show an endoscope and a catheter, respectively, provided with an electric power unit which supplies an electric current to driving member 42 to heat the member. Driving member 42, arranged in insertion section 12 of endoscope 10 or catheter 2, is connected to electric power unit 48 through a pair of lead wires 46. On-off switch 50 is connected to one of the lead wires. In endoscope 10 shown in FIG. 18, the lead wires are incorporated into a cable connecting the operating section with light source unit 52. Electric power unit 48 is arranged at the side of light source unit 52.

The insertion section of the endoscope or catheter may be formed of an elastic material having a large restitution force. With such a structure, plastic deformation of the driving member can be corrected further efficiently by the restitution force of the tube and the elasticity of the elastic member.

Further, in the endoscope using the medical tube of the invention as the insertion section, the elastic member may be formed by the image-guide fiber, light-guide fiber, or other member formed of resin or rubber, that are arranged in the insertion section.

What is claimed is:

1. A medical tube comprising:
   a flexible tube;
   an elastic member embedded in a wall of the flexible tube, for keeping the flexible tube straight, the elastic member being formed of a high-elastic alloy having a transformation temperature at which the alloy transforms in phase from a martensite structure to an austenite structure at a temperature lower than that of a human body; and
   a driving member arranged in the flexible tube for curving the tube, and wherein the driving member includes a shape memory alloy having a transformation temperature at which the alloy transforms in phase from a martensite structure to an austenite structure at a temperature higher than that of a human body.

2. The tube according to claim 1, wherein said elastic member is coil-shaped.

3. The tube according to claim 1, further comprising storage means extending along the whole length of the flexible tube, and said tube containing the driving member therein, and wherein the driving member forms a bent shape when the storage means is supplied with water having a temperature above that at which the driving member shape memory alloy transforms to the austenite structure.

4. The tube according to claim 1, further comprising an electric power unit connected to the driving member, said electric power unit supplying an electric current to the driving member so as to heat the member.

5. The tube according to claim 1, wherein said flexible tube has a multi-lumen structure.

6. The tube according to claim 1, wherein the elastic force F2 of said elastic member required to displace the elastic member by $\Delta l$ is greater than a force F1 required to displace the driving member by $\Delta l$, when said driving member has the martensite structure, and smaller than a force F3 required to displace the driving member by $\Delta l$ when said driving member has the austenite structure.

7. The medical tube of claim 1, wherein said wall of said flexible tube is an outer wall thereof.

8. The medical tube of claim 7, wherein said outer wall is a peripheral wall of said flexible tube.

9. The tube according to claim 8, further comprising a driving member arranged in the flexible tube, for curving the tube, and wherein the driving member includes a shape memory alloy having a transformation temperature at which the alloy transforms in phase from a martensite structure to an austenite structure at a temperature higher than that of a human body.

10. The tube according to claim 9, further comprising storage means extending along the whole length of the flexible tube, and said tube containing the driving member therein, and wherein the driving member forms a bent shape when the storage means is supplied with water having a temperature above that at which the driving member shape memory alloy transforms to the austenite structure.

11. The tube according to claim 10, wherein said elastic member is coil-shaped.

12. An endoscopic tube comprising:
a flexible tube;
a driving member arranged in the flexible tube for curving the flexible tube, said driving member including a shape memory alloy having a transformation temperature at which the alloy transforms in phase from a martensite structure to an austenite structure at a temperature higher than that of a human body; and
an elastic member embedded in a wall of the flexible tube, said elastic member comprising a high-elastic alloy having a transformation temperature from a martensite structure to an austenite structure which is lower than the temperature of a human body, said elastic member keeping the flexible tube straight as long as said driving member is not heated to said temperature at which it transforms from the martensite structure to the austenite structure.

* * * * *